United States Patent [19]

Ojima et al.

[11] Patent Number: 5,018,847
[45] Date of Patent: May 28, 1991

[54] OBSERVATION AND/OR CULTIVATION INSTRUMENT FOR CELLS

[75] Inventors: Satoshi Ojima; Tsuneo Hiraide, both of Tokyo, Japan

[73] Assignee: Asahi Kogaku Kogyo Kabushiki Kaisha, Tokyo, Japan

[21] Appl. No.: 406,320

[22] Filed: Sep. 12, 1989

[30] Foreign Application Priority Data

Sep. 13, 1988 [JP] Japan .................. 63-229257

[51] Int. Cl.$^5$ .................. G02B 1/00; G02B 21/34
[52] U.S. Cl. .................. 350/534; 350/536
[58] Field of Search .................. 350/534–536; 356/244, 246

[56] References Cited

U.S. PATENT DOCUMENTS

| | | |
|---|---|---|
| 1,994,483 | 10/1932 | Ott . |
| 2,328,585 | 1/1941 | Rooney . |
| 2,660,091 | 9/1948 | McCallum . |
| 3,904,781 | 9/1975 | Henry .................. 356/244 |
| 4,113,500 | 9/1978 | Ebihara et al. . |
| 4,149,894 | 4/1979 | Ebihara et al. . |
| 4,183,614 | 1/1980 | Feldman .................. 350/535 |
| 4,761,366 | 8/1988 | Nakajima et al. . |

FOREIGN PATENT DOCUMENTS 1366588  9/1974  United Kingdom .

OTHER PUBLICATIONS

Copy of Japanese Patent Abstract, vol. 12, No. 479 (Asako) (12-14-88).
Copy of Japanese Patent Abstract, vol. 10, No. 71 (Oda) (3-20-86).
Copy of Japanese Patent Abstract, vol. 12, No. 139 (Innami) (4-27-88).
Copy of European Search Report (11-16-89).
Takada, N. et al., "Cell Affinity of Synthesized Hydroxyapatite Sintered Ceramics", *Nihon Univ. Sch. Dent.*, vol. 26, No. 3, pp. 256-264 (1984).
Iijima, K. et al., "Dynamics of MC3T3-E1 Osteogenic Cell Line on Sintered Hydroxyapetite Ceramics", *Tohoku Dental Univ. J.*, vol. 15(1), pp. 15-24 (1988).

*Primary Examiner*—Jon W. Henry
*Attorney, Agent, or Firm*—Sandler, Greenblum & Bernstein

[57] ABSTRACT

An instrument for observation and/or cultivation of cells which has a ceramic coating having a good biocompatibility on a surface thereof to be contacted with said cells. The cells on the instrument of the present invention can be cultivated under the conditions similar to those in vivo, and also can be observed in an optical microscope. The instrument can be sterilized with any sterilization process well-known in this field of technology.

15 Claims, No Drawings

OBSERVATION AND/OR CULTIVATION INSTRUMENT FOR CELLS

BACKGROUND OF THE INVENTION

1. Field of the Invention

The present invention relates to instruments for use in the observation and/or cultivation of cells such as cells of animals and plants, as well as cells of microorganisms. The instrument has different forms depending upon their desired use, and may include, for example a slide or slide glass, a so-called "Schale" or petri dish, or a cultivation container.

2. Description of Related Art

Hitherto, it is well known in the fields encompassing biology, microbiology, and immunology to adhere cells to a wall of a glass or plastic container or to incubate the cells in suspension in the container. However, a problem arises in that some of the cells can not adhere to the glass or plastic container and/or can not be incubated in suspension.

To avoid such problems, it is also well known prepare a solid culture medium from collagen, agar or similar materials in the glass or plastic container and to incubate cells on the medium surface or in the medium. However, while solid culture medium are widely utilized, there are several disadvantages. For example, there are cells which can not adhere to the solid medium, such as collagen or agar medium. Further more there are cells which can spread over the entire medium and such widely spread cells can not be easily observed in an optical microscope. Further, while the instrument and the solid medium must be aseptically stored for a long period from the preparation of the solid medium to the use thereof, it is impossible to apply sterilization, such as gas sterilization and the like, to a solid medium. Restriction of the sterilization process is an important problem.

Recently, to avoid the above-discussed prior art problems, there has been studied and attempts have been made to develop and fabricate ceramics having biocompatibility into an article, and then to cultivate cells on the article. However, these ceramic articles are not suitable for observing cells in an optical microscope, because they are impermeable to light. In addition, these articles tend to be crushed or damaged, are handled with difficulty, and require increased fabrication costs. Also, these articles have a problem that in use, they must be fixed on or in another culture container.

Therefore, it is an object of the present invention to provide an improved which is suitable for observing and/or cultivating cells, and amongst other things does not restrict the types of cells used, the methods of the sterilization used, the methods of culture used and therefore can be widely utilized with satisfactory results.

SUMMARY OF THE INVENTION

According to the present invention, an instrument for observation and/or cultivation of cells is provided which includes a ceramic coating having good biocompatibility, i.e., compatibility or affinity with a living body or organism, with the ceramic coating being applied to a surface of the instrument that is be contacted with the cells.

DESCRIPTION OF THE PREFERRED EMBODIMENTS

The observation and/or cultivation instrument according to the present invention may be produced from any materials which are conventionally used for the same purpose in the prior art. Preferably, the instrument may be produced from a metal, plastic or glass material. Among these materials, specific materials having a light permeability, i.e., optically transparent or translucent materials, such as plastic and glass materials, are advantageously used as a matrix material of the instrument, especially when the cultivated cells on the instrument are intended to be observed in an optical microscope.

The instrument according to the present invention may have any desired configuration. Typical examples of useful configurations include those which are generally used in instruments for the observation and cultivation of the cells, for example, a plate, a dish, a flask, a tube, a cylinder, and the like which may be further modified, if desired.

The instrument of the present invention is characterized by having, on a specific surface thereof, a coating of the selected ceramic material. The ceramic material to be coated on the instrument to form a ceramic coating is preferably selected from any conventional ceramic material, such as zirconia, alumina, calcium phosphate type materials and the like. More preferably, calcium phosphate type materials, and most preferably hydroxyapatite, are used in the formation of the ceramic coating.

The formation of the ceramic coating may be carried out by using any conventional coating process, such as a sputtering process, an ion cluster beam process, a flame spray coating process, a plasma spray coating process and the like. Among these coating processes, the flame spray coating and plasma spray coating processes are preferably used because they ensure obtaining a controlled, sufficiently even thickness of the resulting ceramic coating and other advantages.

The thickness of the ceramic coating may be widely varied depending upon various factors such as a specific material of the coating, a specific use of the instrument and the like. A thickness of the ceramic coating in the range of about 1 to 100 $\mu$m is considered to be appropriate, since the resulting ceramic coating can exhibit a sufficient light permeability to observe the cells on the coating in an optical microscope.

Since the observation and/or cultivation instrument of the present invention, as described above, has on a surface thereof that is to be contacted with cells a coating of a ceramic material having good biocompatibility, it becomes possible to cultivate cells under conditions similar to those in vivo. Further, if the matrix material is selected from those having a light permeability, such as glass and plastics, and also a ceramic coating having a thickness of 100 $\mu$m or less is applied to a selected surface of the matrix material, the resulting instrument is particularly suitable for observing cells on the instrument in an optical microscope especially because the instrument shows a sufficient light permeability to inspect the cells in the microscope. Furthermore, since the instrument of the present invention is constituted of a matrix material and a ceramic coating applied thereto, sterilization can be freely performed by using various sterilization processes such as gas sterilization, $\gamma$-ray sterilization, autoclave sterilization, dry heat sterilization and the like, and also the sterilization operation is easy and can be finished within a short period of time. In addition to these advantages of the sterilization, it is also possible to easily handle and store the sterilized instrument under aseptic conditions. Furthermore, according to the present invention, a ceramic coating can be freely applied to all kinds of observation and/or cultivation instrument, for example, by coating a bottom portion of a glass-made petri dish with a thin layer of the selected ceramic material. Additionally, the production cost of the instrument can be notably reduced as compared with the cost of conventional fabrication, such as the abrasive finishing etc. of the ceramic article. The petri dish with the ceramic coating can be used without first being fixed in another culture instrument.

The present invention will be further described with reference to working examples thereof, to which the present invention is not restricted.

EXAMPLE 1

Powders of hydroxyapatite were produced by dropwise adding a solution of phosporic acid to a slurry of calcium hydroxide, spray drying the resulting slurry to obtain the powders of particle size of 15 to 25 $\mu$m, and then sintering them at 1200° C.

A coating of hydroxyapatite having a thickness of 5 to 10 $\mu$m was applied to a slide glass designed for optical microscopic inspection by a flame spray coating process at a spray distance of 15 cm, using a propylene pressure of 70 psi and an oxygen pressure of 90 psi.

V79 cells originated in Chinese hamster were passage cultivated in an Eagle's MEM (minimum essential medium) culture solution containing 10% of fetal bovine serum. The cultivated V79 cells were treated with 0.1% trypsin solution, suspended therein, and applied in a density of five cells per square centimeter onto a surface of the separately prepared ceramics-coated slide glass. The V79 cells were cultivated in the Eagle's MEM culture solution containing 10% of fetal bovine serum for one week. The thus cultivated V79 cells were inspected with the naked eye to confirm that the cells could form colonies satisfactorily as in the prior art process and also that the number of the formed colonies is substantially equal to that of the prior art process.

We claim:

1. An instrument for cultivation and observation of cells comprising a transparent substrate including a biocompatible ceramic coating, said biocompatible ceramic coating including a surface to be contacted with the cells, and said biocompatible ceramic coating being sufficiently thin and of a sufficiently even thickness to permit observation of the cells on the biocompatible ceramic coating in an optical microscope.

2. The instrument according to claim 1, wherein said substrate comprises a transparent plastic or glass material.

3. The instrument according to claim 1, wherein said substrate is in the form of a plate, dish, flask, tube or cylinder.

4. The instrument according to claim 2, wherein said substrate is in the form of a plate, dish, flask, tube or cylinder.

5. The instrument according to claim 1, wherein said biocompatible ceramic coating comprises zirconia, alumina or a calcium phosphate material.

6. The instrument according to claim 2, wherein said biocompatible ceramic coating comprises zirconia, alumina or a calcium phosphate material.

7. The instrument according to claim 3, wherein said biocompatible ceramic coating comprises zirconia, alumina or a calcium phosphate material.

8. The instrument according to claim 5, wherein said calcium phosphate material is hydroxyapatite.

9. The instrument according to claim 7, wherein said calcium phosphate material is hydroxyapatite.

10. The instrument according to claim 1, wherein said biocompatible ceramic coating is a sputtered, ion cluster beam coated, flame spray coated, or plasma spray coated ceramic coating.

11. The instrument according to claim 1, wherein said biocompatible ceramic coating has a thickness of 1 to 100 $\mu$m.

12. The instrument according to claim 2, wherein said biocompatible ceramic coating has a thickness of 1 to 100 $\mu$m.

13. The instrument according to claim 3, wherein said biocompatible ceramic coating has a thickness of 1 to 100 $\mu$m.

14. The instrument according to claim 5, wherein said biocompatible ceramic coating has a thickness of 1 to 100 $\mu$m.

15. The instrument according to claim 9, wherein said biocompatible ceramic coating has a thickness of 1 to 100 $\mu$m.

* * * * *